(12) United States Patent
Huber et al.

(10) Patent No.: US 8,759,002 B2
(45) Date of Patent: Jun. 24, 2014

(54) GENE DOSAGE ANALYSIS

(75) Inventors: Andreas R. Huber, Aarau (CH); Luca Bernasconi, Zurich (CH); Roberto Herklotz, Lugano (CH); Saskia Brunner-Agten, Bern (CH)

(73) Assignee: Kantonsspital Aarau AG, Aarau (CH)

( * ) Notice: Subject to any disclaimer, the term of this patent is extended or adjusted under 35 U.S.C. 154(b) by 0 days.

(21) Appl. No.: 13/146,373

(22) PCT Filed: Jan. 29, 2010

(86) PCT No.: PCT/EP2010/051090
§ 371 (c)(1),
(2), (4) Date: Jul. 26, 2011

(87) PCT Pub. No.: WO2010/086410
PCT Pub. Date: Aug. 5, 2010

(65) Prior Publication Data
US 2012/0094286 A1    Apr. 19, 2012

(30) Foreign Application Priority Data
Jan. 30, 2009    (EP) .................................... 09151698

(51) Int. Cl.
C12Q 1/68       (2006.01)
C12N 15/11      (2006.01)
(52) U.S. Cl.
USPC ........................................ 435/6.11; 536/24.1
(58) Field of Classification Search
None
See application file for complete search history.

(56) References Cited

U.S. PATENT DOCUMENTS

| 2008/0124712 A1* | 5/2008 | Hantash et al. | .................... 435/6 |
| 2008/0193927 A1 | 8/2008 | Mann et al. | |

FOREIGN PATENT DOCUMENTS

| WO | 97/16568 A1 | 5/1997 |
| WO | 98/23778 A1 | 6/1998 |

OTHER PUBLICATIONS

Liu, T.-C.,et al., Molecular basis and hematological characterization of Hb H disease in Southeast Asia, Am. J. Hematol., 45: 293-297. doi: 10.1002/ajh.2830450405, 1994.*
Armour et al., The Detection of Large Deletions or Duplications in Genomic DNA, Hum Mutat, 20(5), 2002.*
Stratagene Gene Characterization Kits (hereinafter, "Stratagene"; see attached, 1988).*
Sun et al., Real-time quantitative PCR analysis for alpha-thalassemia-I of Southeast Asian type deletion in Taiwan, Clinical Genetics, vol. 60, Issue 4, pp. 305-309, 2001.*
Chang JG, Liu TC, Chiou SS, Chen JT, Chen TP, Lin CP, Rapid detection of -a4.2 deletion of a-thalassemia-2 by polymerase chain reaction, Ann Hematol, 69:205-9, 1994.*
NCBI Accession # AE006462 (Aug. 27, 2002).*
Buck et al. (Biotechniques. 1999. 27(3): pp. 528-536).*
Lowe et al. (Nucleic Acids Research, vol. 18, No. 7, p. 1757-1761, 1990).*
Oron-Karni et al., Rapid Detection of the Common Mediterranean a-Globin Deletions/Rearrangements Using PCR, American Journal of Hematology 58:306-310 (1998), Fig. 1.*
Liu, Ta-Chin, et al., "Molecular Basis and Hematological Characterization of Hb H Disease in Southeast Asia", American Journal of Hematology, 1994, pp. 293-297, vol. 45.
Bowden, D. K., et al., "A PCR-based strategy to detect the common severe determinants of a thalassaemia", British Journal of Haematology, 1992, pp. 104-108, vol. 81.
Liu, Y. T., et al., "Rapid detection of α-thalassaemia deletions and α-globin gene triplication by multiplex polymerase chain reactions", British Journal of Haematology, 2000, pp. 295-299, vol. 108, No. 2.
Heid, Christian A., "Real Time Quantitative PCR", Genome Methods, 1996, pp. 986-994, vol. 6, No. 10.
International Search Report for International Application No. PCT/EP2010/051090 dated Apr. 21, 2010.
J.A.L. Armour, et al., The Detection of Large Deletions or Duplications in Genomic DNA, Human Mutation, vol. 20, pp. 325-337, 2002.
Mircea Schneider, et al., Detection of Exon Deletions Within an Entire Gene (CFTR) by Relative Quantification on the Lightcycler, Clinical Chemistry, vol. 52, No. 11, pp. 2005-2012, 2002.
Franziska Joncourt, et al., Rapid Identification of Female Carriers of DMD/BMD by Quantitative Real-Time PCR, Hum Mutat, 2004, vol. 23, No. 4, p. 385.
Kunihiro Fujii, et al., Mutation Detection by Taqman-Allele Specific Amplification: Application to Molecular Diagnosis of Glycogen Storage Disease Type IA and Medium-Chain Acyl-Coa Dehydrogenase Deficiency, Human Mutation, vol. 15, pp. 189-196, 2000.
H. Das, et al., Quantitation of FAS and FAS Ligand Gene Expression in Human Ovarian, Cervical and Endometrial Carcinomas Using Real-Time Quantitative RT-PCT,British Journal of Cancer, Vol, 82, No. 10, 2000, pp. 1682-1688.
Ruchanee Ausavarungnirun, et al., Detiction of Globin Chains in the Cord Blood by ELISA (Enzyme-Linked Immunosorbent Assay): Rapid Screening for -Thalassemia 1 (Southeast Asion Type), American Journal of Hematology, vol. 57, 1998, pp. 283-286.
Andreas R. Huber, et al., Anomale Hämoglobine: Erscheinungsbilder Und Abklärung, Hemoglobines anormales: tableaux cliniques et diagnostic, Schweiz Med Forum, vol. 4, 2004, pp. 921-926.
Ko TM, et al., Carrier Detection and Prenatal Diagnosis of Alpha-Thalassemia of Southeast Asian Deletion by Polymerase Chain Reaction, Hum Genet, Jan. 1009, vol. 88, No. 3, p. 245.
R. Herklotz, et al., Hamoglobinopathien-Klinik Und Diagnostik Von Thalassamien und Anomalen Hamoglobinen, 2006, pp. 35-46.
Jan-Gowth Chang, et al., Rapid Diagnosis of α-Thalassemia-1 of Southeast Asia Type and Hydros Fetalis by Polymerase Chain Reaction, vol. 78, No. 3, 1991, pp. 853-854.
Lemuel J. Bowie, et al. Detection of α-Thalassemias by Multiplex Polymerase Chain Reaction, Clinical Chemistry, vol. 40, No. 12, 1994, pp. 2260-2266.

* cited by examiner

Primary Examiner — Christopher M Babic
Assistant Examiner — Aaron Priest
(74) Attorney, Agent, or Firm — Sughrue Mion, PLLC

(57) ABSTRACT

The present invention relates to methods of detecting the presence of a genetic polymorphism within two or more closely linked, homologous genes, for example α-thalassemia, in a sample using RT-PCR by subjecting the sample to separate amplification reactions using (a) a pair of forward and reverse primers specific for the head region of each of said two or more closely linked, homologous genes and (b) a pair of forward and reverse primers specific for the tail region of each of said two or more closely linked, homologous genes; and detecting and quantitating the amplification products relative to a control product.

6 Claims, 4 Drawing Sheets

Figure 3.

| | Genotype | Diagnosis | Clinic |
|---|---|---|---|
| α2 α1   α2 α1<br>5' ▰▰ / ▰▰ 3' | αα/αα | normal | |
| ▱▰ / ▰▰ | αα/αα | α⁺-thalassemia heterozygote | Unapparent form |
| ▱▱ / ▰▰ | – –/αα | a⁰-thalassemia heterozygote | Thalassemia minor |
| ▱▰ / ▱▰ | – α/– α | α⁺-thalassemia homozygote | Thalassemia minor |
| ▱▱ / ▱▰ | – –/– α | α⁺/α⁰-thalassemia mixed heterozygote | HbH disease |
| ▱▱ / ▱▱ | – –/– – | α⁰-thalassemia homozygote | HbBart's hydrops fetalis Syndrom |

Figure 4:

| | | allele copy number | | | |
|---|---|---|---|---|---|
| | | head | | tail | |
| | | $\alpha_2$ | $\alpha_1$ | $\alpha_2$ | $\alpha_1$ |
| wt | | 2 | 2 | 2 | 2 |
| 3.7 het | | 2 | 1 | 1 | 2 |
| 4.2 het | | 1 | 2 ⇒ | 1 | 2 |
| 3.7 homo | | 2 | 0 | 0 | 2 |
| anti 3.7 het | | 2 | 3 | 3 | 2 |
| $\alpha^0$ het | | 1 | 1 ⇒ | 1 | 1 |
| $\alpha^0$ het / 3.7 het | | 1 | 0 | 0 | 1 |
| $\alpha^0$ het / 4.2 het | | 0 | 1 | 0 | 1 |
| 3.7 het / 4.2 het | | 1 | 1 ⇒ | 0 | 2 |
| anti 3.7 homo | | 2 | 4 | 4 | 2 |
| 3.7 het / anti 3.7 het | | 2 | 2 | 2 | 2 |
| 4.2 homo | | 0 | 2 | 0 | 2 |
| 4.2 het / anti 3.7 het | | 1 | 3 | 2 | 2 |
| $\alpha^0$ het / anti 3.7 het | | 1 | 2 ⇒ | 2 | 1 |
| anti 3.7 homo | | 2 | 4 | 4 | 2 |

SEQUENCE LISTING

<160> NUMBER OF SEQ ID NOS: 20

<210> SEQ ID NO 1
<211> LENGTH: 22
<212> TYPE: DNA
<213> ORGANISM: Homo sapiens

<400> SEQUENCE: 1
cctcctccac ctaatacata tc                22

<210> SEQ ID NO 2
<211> LENGTH: 16
<212> TYPE: DNA
<213> ORGANISM: Homo sapiens

<400> SEQUENCE: 2
aggtaggcag tcctct                       16

<210> SEQ ID NO 3
<211> LENGTH: 16
<212> TYPE: DNA
<213> ORGANISM: Homo sapiens

<400> SEQUENCE: 3
ctggccctca actgat                       16

<210> SEQ ID NO 4
<211> LENGTH: 19
<212> TYPE: DNA
<213> ORGANISM: Homo sapiens

<400> SEQUENCE: 4
aaataacgaa gacaccgtc                    19

<210> SEQ ID NO 5
<211> LENGTH: 16
<212> TYPE: DNA
<213> ORGANISM: Homo sapiens

<400> SEQUENCE: 5
gacggggttt ctccat                       16

```
<210> SEQ ID NO 6
<211> LENGTH: 16
<212> TYPE: DNA
<213> ORGANISM: Homo sapiens

<400> SEQUENCE: 6
ggtgaggaag gaaggg                                              16

<210> SEQ ID NO 7
<211> LENGTH: 20
<212> TYPE: DNA
<213> ORGANISM: Homo sapiens

<400> SEQUENCE: 7
ctccaaatac cgttaagctg                                          20

<210> SEQ ID NO 8
<211> LENGTH: 17
<212> TYPE: DNA
<213> ORGANISM: Homo sapiens

<400> SEQUENCE: 8
attgttggca cattccg                                             17

<210> SEQ ID NO 9
<211> LENGTH: 21
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n = Fluorescein-modified adenine

<400> SEQUENCE: 9
actaaccctg gtcaccttga n                                        21

<210> SEQ ID NO 10
<211> LENGTH: 21
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n = LC Red 640 modified cytosine
<220> FEATURE:
<221> NAME/KEY: misc_feature
<222> LOCATION: (21)..(21)
<223> OTHER INFORMATION: n = phosphate-modified guanine

<400> SEQUENCE: 10
ncctcgtcca cacctccaga n                                        21

<210> SEQ ID NO 11
<211> LENGTH: 24
<212> TYPE: DNA
<213> ORGANISM: Homo sapiens
<220> FEATURE:
<221> NAME/KEY: misc_feature
<222> LOCATION: (24)..(24)
<223> OTHER INFORMATION: n = Fluorescein-modified cytosine

<400> SEQUENCE: 11
tcacccttgg taaacaccta tggn                                     24

<210> SEQ ID NO 12
<211> LENGTH: 16
<212> TYPE: DNA
```

```
<213> ORGANISM: Homo sapiens
<220> FEATURE:
<221> NAME/KEY: misc_feature
<222> LOCATION: (1)..(1)
<223> OTHER INFORMATION: n = LC Red 640 modified guanine
<220> FEATURE:
<221> NAME/KEY: misc_feature
<222> LOCATION: (16)..(16)
<223> OTHER INFORMATION: n = phosphate-modified thymine

<400> SEQUENCE: 12
nccctctgcc tgcgtn                                              16

<210> SEQ ID NO 13
<211> LENGTH: 18
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n = Fluorescein-modified cytosine

<400> SEQUENCE: 13
ggtctcgaac tcccgacn                                            18

<210> SEQ ID NO 14
<211> LENGTH: 16
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n = LC Red 640 modified adenine
<220> FEATURE:
<221> NAME/KEY: misc_feature
<222> LOCATION: (16)..(16)
<223> OTHER INFORMATION: n = phosphate-modified cytosine

<400> SEQUENCE: 14
ngctgatcca cccgcn                                              16

<210> SEQ ID NO 15
<211> LENGTH: 27
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n = Fluorescein-modified guanine

<400> SEQUENCE: 15
ccttcctggt ctttgaataa agttgan                                  27

<210> SEQ ID NO 16
<211> LENGTH: 17
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n = LC Red 640 modified guanine
<220> FEATURE:
<221> NAME/KEY: misc_feature
<222> LOCATION: (17)..(17)
<223> OTHER INFORMATION: n = phosphate-modified thymine

<400> SEQUENCE: 16
ngcagcagcc tgtgtgn                                             17

<210> SEQ ID NO 17
```

```
<211> LENGTH: 20
<212> TYPE: DNA
<213> ORGANISM: Homo sapiens

<400> SEQUENCE: 17
acacaactgt gttcactagc                                                   20

<210> SEQ ID NO 18
<211> LENGTH: 20
<212> TYPE: DNA
<213> ORGANISM: Homo sapiens

<400> SEQUENCE: 18
caacttcatc cacgttcacc                                                   20

<210> SEQ ID NO 19
<211> LENGTH: 34
<212> TYPE: DNA
<213> ORGANISM: Homo sapiens
<220> FEATURE:
<221> NAME/KEY: misc_feature
<222> LOCATION: (34)..(34)
<223> OTHER INFORMATION: n = Fluorescein-modified adenine

<400> SEQUENCE: 19
aaacagacac catggtgcac ctgactcctg aggn                                   34

<210> SEQ ID NO 20
<211> LENGTH: 29
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n = LC Red 640 modified adenine
<220> FEATURE:
<221> NAME/KEY: misc_feature
<222> LOCATION: (29)..(29)
<223> OTHER INFORMATION: n = phosphate-modified adenine

<400> SEQUENCE: 20
nagtctgccg ttactgccct gtggggcan                                         29
```

GENE DOSAGE ANALYSIS

CROSS REFERENCE TO RELATED APPLICATIONS

This application is a National Stage of International Application No. PCT/EP2010/051090, filed Jan. 29, 2010, which claims priority from European Patent Application No. 09151698.9, filed Jan. 30, 2009, the contents of all of which are incorporated herein by reference in their entirety.

FIELD OF THE INVENTION

The present invention relates to methods for the differential quantitative detection of multiple, closely linked genes, in particular to methods that allow rapid and accurate genotyping of the alleles of the highly homologous α-chain hemoglobin genes, the globin genes α1 and α2.

BACKGROUND

Rapidly evolving genotyping techniques are being used in an attempt to identify the genetic basis of hereditary diseases and to establish a genotype/phenotype correlation, which in turn may allow for a more predictive molecular diagnosis. Yet, most hereditary diseases are genetically very complex and often involve multiple allelic combinations, which may not always show a disease-specific phenotype. In such cases, genotyping of all allelic variants is necessary to be able to distinguish between e.g. non-carriers and disease carriers. Only knowledge of the exact genotype of an individual will allow for an accurate prognosis of the inheritance pattern, an accurate prediction of disease-related symptoms to be expected as the disease progresses as well as an accurate therapy for the individual.

Such diseases include all genetic diseases based on the multiplication of a part of the genome due to unequal crossover events between homologous chromosomes, leading to homologous sequence clusters (duplications) and deletions on a chromosome (FIG. 1). Such diseases include for example spinal muscular atrophy (SMA), diverse microtriplications, and thalassemia. Thalassemia, for example, is a common genetic disorder, which leads in its most moderate form to a hypochromic microcytic anaemia due to impaired hemoglobin formation. The clinical outcome of more severe cases leads to very severe anemia or hydrops fetalis. Depending on the underlying genetic defects, thalassemia is classified into β-thalassemia and α-thalassemia. In β-thalssemia the majority of cases are due to point or raster mutations in the β-globin-locus on chromosome 11, which contains a single gene encoding the β-globin chains. The α-thalassemias, which are classified into α-thalassemia, $\alpha^+$-thalassemia and $\alpha^0$-thalassemia, are mainly the result of deletions on chromosome 16, which contains at its telomeric region two highly homologous and closely linked genes (α1- and α2-gene) encoding the α globin chains. The duplicated alpha-globin genes α1 and α2 are embedded within two markedly homologous regions that extend for approximately 4 kb. During meiosis, misalignment of chromosome homologs followed by reciprocal recombination at three highly homologous segments, named X, Y, and Z, results in various deletion-duplication events (FIG. 2).

The causes of α-thalassemia, $\alpha^+$-thalassemia and $\alpha^0$-thalassemia, are the deletion or dysfunction of one or both α1 and α2 genes, respectively.

Deletional $\alpha^+$-thalassemia results from loss of one of the two α-globin genes (αα/-α), e.g. by reciprocal recombination between the Z region, which are 3.7 kb apart, or between the X region, 4.2 kb apart, giving rise to the $-\alpha^{3.7kb}$ and $-\alpha^{4.2kb}$ deletion, respectively. FIG. 2 is a schematic illustration of the unequal crossover events leading to those deletions (filled squares represent the functional active genes α1 and α2 of the alpha globin gene cluster and blank squares represent the homologues X-, Y- and Z-boxes and one of the two pseudoglobingenes, i.e. Ψα1). Heterozygote carriers of $\alpha^+$-thalassemia resulting from the combination of a deletional $\alpha^+$-thalassemia (-α) and a wt (αα) (also known as α-thalassemia silent carrier (-α/αα)) may have a silent hematologic phenotype instead homozygote carriers ((-α/-α)) present a moderate thalassemia-like hematologic picture (see e.g. Herklotz et al, Ther Umsch, 2006, 63 (1), p. 35).

$\alpha^0$-Thalassemia may be caused by extended deletions varying from 5.2 kb to 25 kb and more resulting in deletion or dysfunction of both, the α1 and the α2 genes (homozygotes (--/--) or heterozygotes (αα/--)), e.g. $-\alpha^{SEA}$, $-\alpha^{TAI}$, $-\alpha^{FIL}$, $-\alpha^{MED}$, $-(\alpha)^{20.5kb}$. About 30 different such $\alpha^0$-thalassemia deletions have been reported to date.

The outcomes of the α-thalassemias are manifold and the severity is correlated with the number of affected α-globin loci, i.e. the exact nature of the gene deletion, as illustrated in FIG. 3 (filled boxes: α-globin gene(s) present, blank boxes: α-globin gene(s) deleted).

The phenotypes of α-thalassemia have two clinically significant forms, which are Hb Bart hydrops fetalis (Hb Bart) syndrome and hemoglobin H (HbH) disease. In Hb Bart, all four α-globin alleles are deleted or inactivated (--/--). It is the most severe form and is characterized by fetal onset of generalized edema, with death in the neonatal period being almost inevitable. HbH disease is a result of deletion or dysfunction of three of the four α-globin alleles (--/-α). It is characterized by microcytic hypochromic hemolytic anemia, hepatosplenomegaly, mild jaundice, and sometimes bone and heart changes.

The milder forms of thalassemia ((-α/-α), (--/αα) lead to hematologic changes, usually without any clinical symptoms. However, for the so called "silent" thalassemia the exact diagnosis is still very important (αα/-α).

It is estimated that there are at least 200 million people affected worldwide. In addition, 300'000-400'000 severely affected infants are born every year, more than 95% of which occur in Asia, India, and the Middle East.

Current testing for α-thalassemia is based on an algorithm of exclusion-diagnosis (i.e. to exclude iron deficiency, β-thalassemia, the haemoglobinopathies and hemolytic anemia), which requires a wide range of procedures such as hematologic testing of red blood cell indices, peripheral blood smear, supravital staining to detect RBC inclusion bodies, qualitative and quantitative hemoglobin analysis, bone marrow examination, and in vitro synthesis of radioactive-labeled globin chains in affected individuals. Final proof for the presence of an α-thalassemia is obtained using biomolecular diagnostics (Huber et al., Swiss Medical Forum, 2004). This includes polymerase chain reaction (gap-PCR) amplification of the normal α1 and α2 or hybrid α2/α1 globin genes (Chang et al., Blood, 1991, 78 (3), 853; Ko et al., Hum Genet, 1992, 88 (3), 245), enzyme-linked immuno-sorbent assays (ELISA) for the detection of zeta-globin chains in circulation (Ausavarungnirun et al., Am J Hematol, 1998, 57 (4), 283) and hybridization assays with α-strips.

The Real-time Quantitative PCR technique (RT-PCR) has been applied for different investigations including pathogen detection, allelic discrimination, gene expression and gene regulation (Bowie et al., Clin Chem, 1994, 40 (12), 2260; Das et al., Br J Cancer, 2000, 82 (10), 1682; Fujii et at., Mutat, 2000, 15 (2), 189), as well as the detection of duplications and deletions, e.g. in Duchenne and Becker muscular dystrophies, cystic fibrosis and neuroblastomas (Joncourt et al., Hum Mutat 2004, 23 (4): 385), detection of exon deletions within an entire gene (CFTR) by relative quantification on the Light-Cycler (Schneider M. et al., American Association for Clinical Chemistry 2006, 52: 11) Quantification of MYCN, DDX1 and NAG gene copy number in neuroblasotma using a real-time quantitative PCR assay (De Preter K. et al., Mod Pathol 2002, 15 (2): 159-166). However, while RT-PCR has also been applied for the detection of α-thalassemia (Armour et al., Hum Mutat, 2002, 20 (5), 325), current methods only allow for detection of several restricted mutations such as the southeast Asian type deletion, or a group of e.g. three different deletions ($-\alpha^{3.7kb}$, $-\alpha^{SEA}$ and $-\alpha^{MED}$).

Clearly, current technologies are labor-intensive and/or time-consuming and in case of hereditary diseases linked to repeat gene clusters, i.e. multiple genes, such as α-thalassemia, may still not provide an accurate analysis of all variants of the diseases.

Thus, there is a great need for a general, rapid and efficient screening method, which is completely standardized and suitable for routine laboratory, which allows the differential quantitative detection of multiple homologous gene loci underlying a specific hereditary disease, such as the ones mentioned hereinabove.

Applicants have now designed a new screening method using multiple primer sets performing only one single RT-PCR run, which enables classification of the genotype of an individual affected by such a hereditary disease. Quantification of each of the amplicated gene regions in reference to a control, preferably one or several endogenous control (reference gene), and particularly the relationship between each of the amplicated regions allows the well-defined identification of the genotype of the individual. In case of an aberrant genotype, subsequent analysis, e.g. sequencing, allows to further characterize the exact nature and location of the mutation.

The new method according to the invention is applicable to any genetic disorder based on multiple homologous gene loci. For example, applicants have shown that the new screening method allows for a clear classification of the genotype of the α-thalassemia of any patient performing one single RT-PCR run. The quantification of each of the amplificated α-globin-gene regions and particularly the relationship between those regions will allow for the determination of the real prevalence of α-thalassemia detecting all carriers, which may otherwise be subject to mis- or nondiagnosis. This is a particularly important tool with respect to genetic counseling in general and/or prenatal diagnosis.

SUMMARY OF THE INVENTION

The present invention provides in a first aspect a method for differential quantitative detection of two or more closely linked, homologous genes in a sample.

More specifically, the present invention provides a method for differential quantitative detection of two or more closely linked, homologous genes in a sample comprising the steps of (i) subjecting the sample to separate amplification reactions using a pair of forward and reverse primers specific for the head region of each of said two or more closely linked, homologous genes and (b) a pair of forward and reverse primers specific for the tail region of each of said two or more closely linked, homologous genes; and (ii) detecting and quantifying the amplification products relative to a control product.

In one embodiment the amplification reactions are performed using RT-PCR, preferably in a single step, more preferably using one or more fluorescence-based hybridisation probes.

In another embodiment, the control product is the amplification product of a control sequence, preferably an endogenous control sequence.

In another aspect, the present invention provides an accurate screening method for carriers of a genetic polymorphism within two or more closely linked, homologous genes in a sample. Thus the present invention also relates to a method of diagnosing an individual by accurate and exact identification of his or her genotype.

In one specific embodiment, the present invention provides a method for accurate quantitative detection of the α gene(s) in carriers of α-thalassemia thereby determining the clinical relevant classification of the α-thalassemias (FIGS. 2, 3). Thus, the present invention provides an accurate screening method for carriers of (deletional) α-thalassemia.

In a preferred embodiment, a method for accurate quantitative detection of the α gene(s) in a biological sample comprises the steps of:
(i) amplifying a first portion of the sample with a pair of forward and reverse primers specific for the head region of α1;
(ii) amplifying a second portion of the sample with a pair of forward and reverse primers specific for the head region of α2;
(iii) amplifying a third portion of the sample with a pair of forward and reverse primers specific for the tail region of α1;
(iv) amplifying a fourth portion of the sample with a pair of forward and reverse primers specific for the tail region of α2; and
(v) detecting and quantifying amplification products relative to a control product.

In one embodiment the detecting step is performed using labelled hybridisation probes.

In another embodiment, the control product is the amplification product of an endogeneous control sequence, such as a housekeeping gene or a sequence related to the gene to be detected, such as the β-gene.

In another aspect, the present invention provides oligonucleotides for use as primers in amplifying the specified regions within the α-globin gene cluster, i.e. the head and tail regions of the α1 and α2 gene. Such oligonucleotides may be designed based on the known non homologous sequence of the head and tail regions of the α1 and α2 gene and are about 10 to about 100 nucleotides in length. In a specific embodiment the oligonucleotides comprise any sequence specific for the head and tail regions of the α1 and α2 gene region, respectively, within the alpha-globin gene cluster as identified by GenBank Accession No. AE006462. In a preferred embodiment the oligonucleotides comprise the non homologous sequences in the alpha-globin gene cluster set forth in SEQ ID NOs: 1-8 and the fluorescence-based hybridisation probes comprise the sequences SEQ ID Nos: 9-16.

In yet a further aspect the present invention provides a kit for differential quantitative detection of two or more closely linked homologous genes to allow for screening and diagnosis of an individual. The kit may include in separate compartments primer pairs according to the invention capable of specifically hybridizing to and amplifying the head and tail regions of the gene in question. The kit may further include appropriately labelled hybridisation probes for detection and a primer pair capable of hybridizing to and amplifying a control sequence.

Thus, in a specific embodiment the present invention provides a kit for the quantitative detection of deletions in the α-globin gene cluster to allow for screening and diagnosis of thalassemia in an individual. The kit may include in separate compartments primer pairs according to the invention capable of specifically hybridizing to and amplifying the head and tail regions of the α1 and α2 genes and optionally labelled hybridisation probes for detection and a primer pair capable of hybridizing to and amplifying a control sequence, such as a region of the β-globin gene sequence.

In yet a further aspect the methods of the invention may be performed using (micro) arrays. Thus the present invention also-provides an array for genotyping polymorphisms based on two or more closely linked, homologous genes using the methods of the invention.

BRIEF DESCRIPTION OF THE FIGURES

FIG. 3. Schematic presentation of the classic deletion forms of the α-thalassemia and the correlation between phenotype and genotype.

FIG. 4. Selected genotypes and ratio patterns.

DETAILED DESCRIPTION OF THE INVENTION

Figure 1:
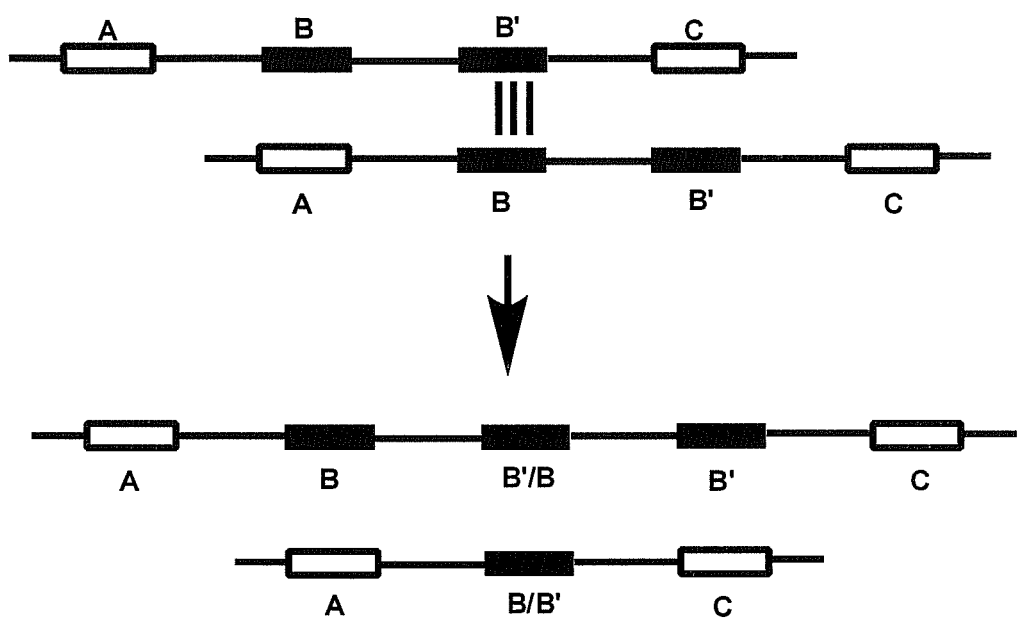
FIG. 1. Unequal crossing over event in a tandem repeat cluster (genome homozygous of the original duplicated chromosome).
Figure 2:
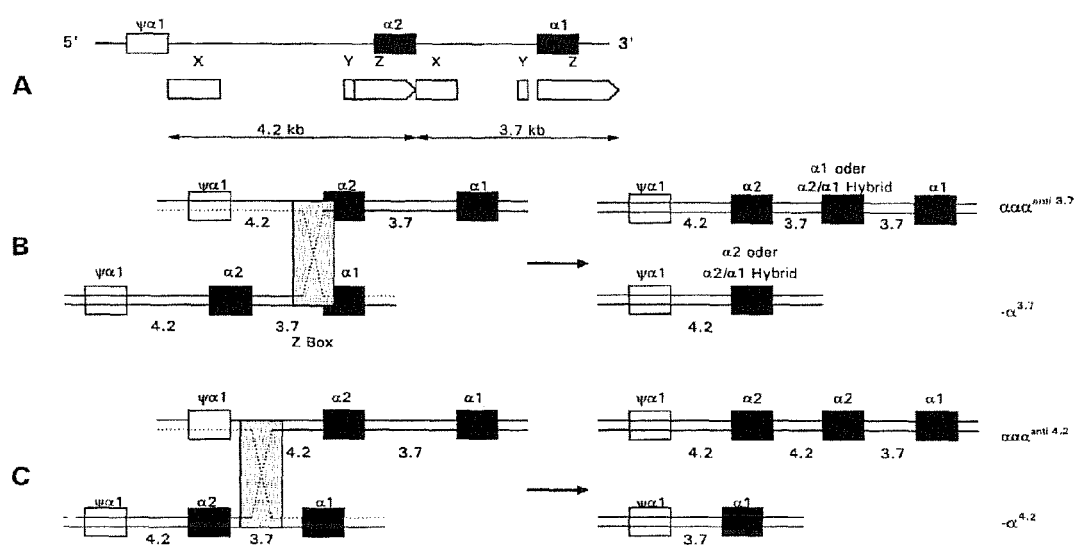
FIG. 2. (A) Structural organisation of the α-globin gene cluster; (B) and (C): unequal crossover events leading to deletional $α^+$-thalassemia.

The present invention was developed in response to a need for a rapid, highly specific, and cost-effective method to genotype individuals carrying multiple, homologous genes linked to a hereditary disease, such as spinal muscular atrophy (SMA), diverse microtriplications, α-thalassemia, and others. Unless otherwise specified the terms used herein are defined according to the general state of the art.

The term "amplification" or "to amplify" as used herein means to increase the number of copies of a nucleic acid molecule. The resulting amplification products are called "amplified products" or "amplicons." An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by techniques known in the art such as electrophoresis, restriction endonuclease cleavage patterns, oligonucleotide hybridization or ligation, and/or nucleic acid sequencing. Other examples of in vitro amplification techniques include Quantitative Real-Time PCR, Reverse Transcriptase PCR, Real-Time Reverse transcriptase PCR, Nested PCR; strand displacement amplification (see U.S. Pat. No. 5,744,311), ligase chain reaction amplification (see EP-A-320 308); gap filling ligase chain reaction amplification (see U.S. Pat. No. 5,427,930), coupled ligase detection and PCR (see U.S. Pat. No. 6,027,889), multiplex ligation dependent probe amplification (MLPA) etc.

The term "Real-time PCR" (RT PCR) as used herein is based on the PCR method and means a method for amplifying and simultaneously quantifying products generated during each cycle of a PCR, which are proportionate to the amount of template nucleic acid prior to the start of PCR. Thus, it enables both detection and quantification (as absolute number of copies or relative amount when normalized to DNA input or additional normalizing genes) of a specific sequence in a DNA sample. Reference is also made to a general review of PCR techniques and to the explanatory note entitled "Quantitation of DNA/RNA Using Real-Time PCR Detection" published by Perkin Elmer Applied Biosystems (1999) and to PCR Protocols (Academic Press New York, 1989) as well as to descriptions given hereinafter.

Quantification within RT PCR is based on the detection of a fluorescent reporter (Lee, 1993; Livak, 1995). This signal changes (increase or decrease) in direct proportion to the amount of PCR product in a reaction. By recording the amount of fluorescence emission at each cycle, it is possible to monitor the PCR reaction during exponential phase where the first significant change in the amount of PCR product correlates to the initial amount of target template.

The fluorescence-monitoring systems for DNA amplification to be employed in the methods of the invention include for example DNA-binding or intercalating agents (such as ethidiumbromide or SYBR® Green I) and probes based on Fluorescence Resonance Energy Transfer (FRET).

The use of double-stranded DNA binding dye chemistry allows to quantitate the amplicon production (including non-specific amplification and primer-dimer complex) by the use of a non-sequence specific fluorescent intercalating agent, such as SYBR-green I, ethidium bromide, or the like (see for example U.S. Pat. No. 6,569,627).

FRET technology (see, for example, U.S. Pat. No. 4,996,143, U.S. Pat. No. 5,565,322, U.S. Pat. No. 5,849,489, and U.S. Pat. No. 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween. The donor and acceptor fluorescent moieties can be attached to the appropriate probe oligonucleotide via a linker arm. The length of each linker arm is important, as the linker arms will affect the distance between the donor and acceptor fluorescent moieties.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength.

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LCT™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Probes based on FRET technology include for example hybridization probes (e.g. LightCycler probes), hydrolysis probes such as TaqMan™ probes (Heid et al, 1996, incorporated herein by reference for its teaching of hydrolysis probes), molecular beacons (Mhlanga, 2001; Vet, 2002; Abravaya, 2003; Tan, 2004; Vet & Marras, 2005, incorporated herein by reference for their teaching of molecular beacons) and scorpion probes (Saha, 2001; Solinas, 2001; Terry, 2002, incorporated herein by reference for their teaching of scorpions).

Oligonucleotides to be used as hybridization probes include a pair of two different oligonucleotides, one of them carrying a FRET Donor, the other FRET acceptor. This pair of probes preferably anneals to an amplification product within no more than 5 nucleotides of each other on the same strand bringing the respective fluorescent moieties into sufficient proximity such that FRET can occur (e.g., within no more than 1, 2, 3, or 4 nucleotides of each other). It is to be understood, however, that other separation distances (e.g., 6 or more nucleotides) are possible provided the fluorescent moieties are appropriately positioned relative to each other (for example, with a linker arm) such that FRET can occur. As with oligonucleotide primers, oligonucleotide probes usually have similar melting temperatures, and the length of each probe must be sufficient for sequence-specific hybridization to occur but not so long that fidelity is reduced during synthesis. Such oligonucleotide probes are generally 10 to 40, preferably 15 to 30 nucleotides in length.

TaqMan™ probes to be used in the present invention are typically single oligonucleotides longer than the primers of the invention (20-30 bases long with a Tm value of 10° C. higher) that contain a fluorescent dye usually on the 5' base, and a quenching dye typically on the 3' base. When irradiated, the excited fluorescent dye transfers energy to the nearby quenching dye molecule. Thus, only upon replication of a template to which a TaqMan™ probe is bound, and cleavage of the probe fluorescence is emitted (proportional to the rate of probe cleavage). Accumulation of PCR products according to the invention is detected by monitoring the increase in fluorescence of the reporter dye. TaqMan™ assay uses universal thermal cycling parameters and PCR reaction conditions.

Molecular beacons may also be used in the methods of the present invention. These also contain fluorescent (FAM, TAMRA, TET, ROX) and quenching dyes (typically DABCYL) at either end but they are designed to adopt a hairpin structure while free in solution to bring the fluorescent dye and the quencher in close proximity for FRET to occur, while annealing while prevent formation of the hairpin structure.

Using Scorpion probes for the present invention, sequence-specific priming and PCR product detection is achieved using a single oligonucleotide. The Scorpion probe maintains a stem-loop configuration in the unhybridised state, having a fluorophore attached to the 5' end and a quenching moiety coupled to the 3' end. The 3' portion of the stem also contains a sequence that is complementary to the extension product of the primer and which binds to its complement upon sequence extension thereby allowing to observe a fluorescence signal.

The real-time PCR reaction can be carried out in a wide variety of platforms including, but not limited to ABI 7700 (ABI), the LightCycler (Roche Diagnostics), iCycler (Rio-Rad), DNA Engine Opticon ContinuousFluorescence Detection System (MJ Research), Mx400 (Stratagene), Chimaera Quantitative Detection System (Thermo Hybaid), Rotor-Gene 3000 (Corbett Research), Smartcycler (Cepheid), or the MX3000P format (Stratagene).

The terms "genome", "genomic sample", "genomic DNA", "genomic (nucleic acid) material" may be used interchangeably and mean the nucleic acid molecules in an organism or cell that are the ultimate source of heritable genetic information of the organism. For most organisms, a genome consists primarily of chromosomal DNA, but it can also include plasmids, mitochondrial DNA, etc. For some organisms, such as RNA viruses, a genome consists of RNA. As used within the present specification, genomic DNA is undigested or intact unless otherwise stated. By "nucleic acid" is meant DNA, RNA, or other related compositions of matter that may include substitution of similar moieties. For example, nucleic acids may include bases that are not found in DNA or RNA, including, but not limited to, xanthine, inosine, uracil in DNA, thymine in RNA, hypoxanthine, and so on. Nucleic acids may also include chemical modifications of phosphate or sugar moieties, which can be introduced to improve stability, resistance to enzymatic degradation, or some other useful property. The genomic material may be isolated from virtually any sample, usually, the sample is a biological or a biochemical sample.

The term "biological sample," as used herein, refers to a sample containing nucleic acid, i.e. genomic material, and is obtained from an organism or from components (e.g., cells) of an organism. The sample may be of any biological tissue or fluid (human or animal), preferably the sample will be a "clinical sample" derived from an individual. Such samples include, but are not limited to, sputum, cerebrospinal fluid, blood, blood fractions such as serum including foetal serum (e.g., SFC) and plasma, blood cells (e.g., white cells), tissue or fine needle biopsy samples, urine, peritoneal fluid, and pleural fluid, or cells there from. Biological samples may also include sections of tissues. A sample containing (or suspected to have) a genomic content may be biological material or any material comprising biological material from which nucleic acids may be prepared and analysed for the qualitative and quantitative presence of particular nucleic acid sequences. Genomic nucleic acid material to be used in the methods of the present invention is preferably in isolated form, i.e. subjected to some preparation prior to its use, which may involve the removal of non-nucleic acid debris as well as suspension/dilution of the pure or isolated nucleic acid material in water or an appropriate buffer. By "pure" or "isolated" in reference to a nucleic acid (e.g. recombinant or cloned DNA isolates, RNA isolates, mixed polymers, oligonucleotides, and chemically synthesized analogs) is meant one which is substantially separated from other cellular components and non-nucleic acid debris, which naturally accompany such nucleic acid.

The term may also embrace suspension/dilution of the pure or isolated nucleic acid material in water or an appropriate buffer.

The term "two or more closely linked, homologous genes" refers to multiple repeat clusters of genes, wherein multiple, i.e. at least two homologous genes are related by expression pattern. For example, with respect to α-thalassemia the α1-, α2-genes represent the "tandem repeat cluster" or "two closely linked genes".

The term "genotype" refers to the genetic constitution of an organism. More specifically, the term refers to the identity of alleles present in an individual. "Genotyping" of an individual or a DNA sample refers to identifying the nature, in terms of nucleotide bases, of the two alleles possessed by an individual at a known polymorphic site. The term "allele" is used herein to refer to different versions of a nucleotide sequence. The term "wild type" or "wt" as used herein refers to the normal, or non-mutated, or functional form of a gene carrying no mutations. A mutation affecting only one allele is called "heterozygous". A "homozygous" mutation is the presence of the identical mutation on both alleles of a specific gene. When both alleles of a gene harbor mutations, but the mutations are different, these mutations are called "compound heterozygous". Thus with respect to α-thalassemia, an individual having (i) all four intact alleles is referred to as "wt" (αα/αα), (ii) one of four alleles deleted is referred to as heterozygote α$^+$-thalassemia (−α/αα), (iii) two of four alleles deleted is referred to as either homozygote a+-thalassemia (−α/−α) or heterozygote a$^0$-thalassemia (−−/αα), (iv) three of four alleles deleted is referred to as compound heterozygote α$^+$/α$^0$-thalassemia (−−/−α), and (v) all four alleles deleted is referred to as homozygote α$^0$-thalassemia (−−/−−).

The term "oligonucleotide" as used herein refers to primers, probes, and oligomer fragments to be detected and is defined as a molecule comprised of two or more deoxyribonucleotides, preferably more than three. Its exact size depends on various factors including the ultimate function or use of the oligonucleotide and will be defined separately.

The term "primer", as used herein, refers to a short single-stranded oligonucleotide capable of hybridizing to a complementary sequence in a DNA sample. A primer serves as an initiation point for template dependent DNA synthesis. Deoxyribonucleotides can be joined to a primer by a DNA polymerase. A "pair of primers", "primer pair" or "primer set" refers to a set of primers including a 5'-upstream or forward primer that hybridizes with the complement of the 5' end of the DNA sequence to be amplified and a 3' downstream or reverse primer that hybridizes with the 3' end of the DNA sequence to be amplified. The term "PCR primer" as used herein refers to a primer used for a PCR reaction.

The term "control sequence" as used herein means a gene or nucleic acid sequence at a consistent expression level which is included as an internal control or standard sequence to ensure that the amplification has progressed, giving rise to an amplified product, herein also termed "control fragment" or "control product". It is designed such that it may be amplified by the same or different primers, preferably different primers, as those used to amplify the target DNA sequence. The size of the amplified control fragment may be the same or different to that of the target DNA sequence. When the product obtained is analysed, for example using fluorescence, the amplified control fragment may be the same or different to that of the target DNA sequence. When the product obtained is analysed, for example using gel electrophoresis, the amplified control fragment is preferably different, such that a separate band is produced on the gel (indicating that the amplification reaction has progressed). The control sequence is preferably an endogeneous control sequence and is present in a known amount in the starting material. Preferred endogenous control sequences are for example housekeeping genes which are typically used for normalization due to their stable expression levels in all cell types. Housekeeping genes are well known and include such genes as phorphobilinogen deaminase, hypoxanthine phosphoribosyltransgerase, δ-aminolevulinate-synthase, β2-microglobulin, albumin, β-actin, glucose-6-phosphate dehydrogenase and the like. Such a control sequence or housekeeping gene may be determined using standard protocols (e.g. Lightcycler® h-Housekeeping gene selection set (Roche)). Alternatively a sequence specific for the gene to be detected may be used as an endogenous control sequence, such as the β-gene sequence in the case of diagnosis of the α-genes of thalassemia. The target and the control sequence may be amplified in separate RT-PCR reactions. Alternatively, the control sequence is amplified together with the target sequence in the same test tube (internal control). It is understood that internal control and gene-specific primers must be compatible (i.e. no cross-hybridization). It is also understood that use of an internal control implies that the RT-PCR products can sufficiently be discriminated, e.g. on the basis of different fluorescence signals. It is further understood that one or more than one control sequences may be used By "complement" and like words, e.g., "complementary" and "complementarity", is meant the complementary sequence to a nucleic acid (RNA, DNA, cDNA) according to standard Watson/Crick pairing rules. Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

The term "stringent conditions" as used herein refers to the washing conditions used in a hybridization protocol and means hybridization will occur only if there is at least 95% and preferably at least 97% identity between the sequences. In general, the washing conditions should be a combination of temperature and salt concentration chosen so that the denaturation temperature is approximately 5-20° C. below the calculated Tm (the melting temperature at which half of the molecules dissociate from their hybridization partners) of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The Tm of such an oligonucleotide can be estimated by allowing 2° C. for each A or T nucleotide, and 4° C. for each G or C.

Suitable stringent hybridization conditions will be well known to those of skill in the art (see, e.g., Molecular Cloning: A Laboratory Manual, 3rd ed., Sambrook et al. eds., Cold Spring Harbor Laboratory Press, 2001; DNA Cloning: A practical Approach, Glover & Hames eds., Oxford University Press, 1996; Nucleic Acid Hybridization: Essential techniques, Ross ed. Wiley, 1998). An example of stringent wash conditions may be 4×SSC (Standard Saline Citrate) at 65° C. Highly stringent wash conditions include, for example, 0.2× SSC at 65° C. The term "deletion" as used herein encompasses a mutation that removes one or more nucleotides from a nucleic acid. Conversely, the term "duplication" refers to a mutation that inserts one or more nucleotides of identical sequence (for the most part) directly next to this sequence in a nucleic acid. In a preferred embodiment, a deletion or duplication involves a segment of four or more nucleotides. With respect to α-thalassemia, a deletion can remove part or all of the α1-, the α2-gene or part or all of both of them (α1/α2).

The term "specific" as used herein in reference to an oligonucleotide primer means that the hybridization sequence of the primer has at least 10 bases of sequence identity with a portion of the nucleic acid to be amplified when the oligonucleotide and the nucleic acid are aligned. An oligonucleotide primer that is specific for a nucleic acid is one that, under the appropriate hybridization or washing conditions, is capable of "specifically hybridizing to and amplifying" the target of interest and not substantially hybridizing to and amplifying nucleic acids which are not of interest. Higher levels of sequence identity are preferred and include at least 80%, at least 85%, at least 90%, at least 95% and more preferably at least 98% sequence identity.

The term "hybridize" or "specifically hybridize" as used herein refers to a process where two complementary nucleic acid strands anneal to each other under appropriately stringent conditions. Hybridizations are typically and preferably conducted with probe-length nucleic acid molecules, preferably 10-100 nucleotides in length, more preferably 10-50 nucleotides in length, most preferably 10-30 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "homologous" with reference to nucleic acid sequences indicates that two or more sequences share a majority of their sequence. Generally, this will be at least about 70% of their sequence and preferably at least 95% of their sequence. Another indication that sequences are substantially identical is if they hybridize to the same nucleotide sequence under stringent conditions (see, e.g., Sambrook et al., Molecular Cloning—A Laboratory Manual, Cold Spring Harbor Laboratory, Cold Spring Harbor, N.Y., 2001). Stringent conditions are sequence-dependent and will be different in different circumstances.

The terms "head" and "tail" as used herein (e.g. in combination with the term "region") refer to nucleotide sequences at either end, i.e. 5' or 3' of a particular gene. The head and tail regions may either be flanking having no overlap with the respective gene or may overlap with the respective end of the gene. In the latter case the ends of the head and tail regions (i.e. the 3' end of the head region and the 5' end of the tail region) either (i) are separated by a gap or (ii) adjoin each other or (iii) are overlapping each other. More specifically, in one embodiment the nucleic acid sequences specific for head and/or tail regions may be specific for a region (i) flanking and overlapping with the respective end of the gene, or (ii) only flanking the respective end of the gene, or (iii) only overlapping with the respective end of the gene or (iv) combinations thereof. The length of the head and tail region for one gene, e.g. the α1-gene, is typically confined by the neighbouring gene, e.g. the α2-gene. According to the convention, single strands of DNA and RNA sequences are written in 5' to 3' direction. Thus with respect to the α-globin genes, the head and tail regions of α1 comprise about nucleotides 163708 to 167099 of the 5'-sequence (i.e. head region) and about nucleotides 167099 to 170335 of the 3'-sequence (i.e. tail region) of the α-globin gene cluster as identified in GenBank Accession No. AE006462. Whereas the head and tail regions of α2 comprise about nucleotides 158640 to 162875 of the 5'-sequence (i.e. head region) and about nucleotides 162875 to 166679 of the 3'-sequence (i.e. tail region) of the α-globin gene cluster as identified in GenBank Accession No. AE006462.

In view of the above it is clear, that the primers may have various different lengths, and that the exact location of the stretch of contiguous nucleotides to which the primer is hybridizing, can vary. Yet, it is important that the sequences to which the forward and reverse primers of each primer pair (for each of the closely linked, homologous genes) anneal are located on either side of the particular position of crossover event within each of said closely linked, homologous genes (that give rise to the various genotypes). For example, when designing primer pairs for amplification of multiple (at least two) closely neighboring genes, each assay consists of two primer pairs for each of the closely linked, homologous genes: a first primer pair located upstream of the estimated breakpoint due to the crossing-over on the first targeted gene (head region) and a second primer pair located downstream of the breakpoint on the first targeted gene (tail region), with the proviso that the primer locations are chosen such that the primer pair located at the tail region of the first gene is not overlapping with the primer pair located at the head region of the second gene of said multiple closely linked, homologous genes. For example, in the case where the multiple closely linked homologous genes represent the α1 and α2 gene of α-thalassemia, the α2 head amplicon is the amplicon upstream of the first gene of these two highly homologous genes, the α2 tail amplicon is downstream of the first gene of these two highly homologous genes, the α1 head amplicon is upstream and the α1 tail amplicon is downstream of the second gene of these two highly homologous genes.

As used herein, the term "amplicon" refers to a polynucleotide sequence amplified within a target sequence, and defined by the distal ends of two primer-binding sites. For use in the present invention the amplicons generated by the various primer pairs may be the same or different.

As used herein, "linked" or "linkage" (as distinguished from the term "operably linked") shall refer to the genetic or physical linkage of loci or genes. Loci or genes are considered genetically linked if the recombination frequency between them is less than about 50% as determined on a single meiosis map. They are progressively more linked if the recombination frequency is about 40%, about 30%, about 20%, about 10% or less, as determined on a single meiosis map. The term "closely linked" means that two genetic loci are typically within 10 centimorgans (cM) of each other. That is, the two associated genetic elements undergo recombination during meiosis with each other at a frequency of less than or equal to about 10%, 9%, 8%, 7%, 6%, 5%, 4%, 3%, 2%, 1%, 0.75%, 0.5%, 0.25% or less. Closely linked loci are expected to co-segregate at least about 90% of the time.

The present invention provides in a first aspect a method for accurate quantitative detection of deletion(s) or duplication(s) of a genetic polymorphism occurring within two or more closely linked, homologous genes in a sample.

More specifically this method comprises
(i) subjecting the sample to separate amplification reactions using (a) a pair of forward and reverse primers specific for the head region of each of said two or more closely linked, homologous genes and (b) a pair of forward and reverse primers specific for the tail region of each of said two or more closely linked, homologous genes, and
(ii) detecting the amplification products relative to a control product.

Thus, in case of two closely linked, homologous genes, the method comprises the steps of:
(i) subjecting the sample to a first amplification reaction using a pair of forward and reverse primers specific for the head region of a first of said two closely linked, homologous genes,
(ii) subjecting the sample to a second amplification reaction using a pair of forward and reverse primers specific for the tail region of said first of said two closely linked, homologous genes,
(iii) subjecting the sample to a third amplification reaction using a pair of forward and reverse primers specific for the head region of a second of said two closely linked, homologous genes,
(iv) subjecting the sample to a second amplification reaction using a pair of forward and reverse primers specific for the tail region of said second of said two closely linked, homologous genes,
(v) detecting amplification products obtained in the reactions of steps (i) to (iv), and optionally quantifying said amplification products relative to a control product.

In a preferred embodiment the amplification reactions used in the methods for detection and quantitation of a genetic polymorphism occurring within two or more closely linked, homologous genes in a sample, are carried out using PCR techniques, preferably using RT-PCR, preferably using (FRET) hybridization probes or hydrolysis probes.

Thus in one specific embodiment, each amplification reaction includes contacting the sample with (a) a pair of forward and reverse primers for the respective portion (head or tail) of a gene (as described hereinabove) to produce the respective amplification product, and (b) a pair of hybridization probes specific for the respective amplification product, of which a first probe of the pair is typically labeled with a donor fluorescent moiety and a second probe of the pair is labeled with a corresponding acceptor fluorescent moiety. The method further includes detecting the presence or absence of FRET between the donor fluorescent moiety of the first probe and the acceptor fluorescent moiety of the second probe. The presence of FRET is (usually) indicative of the presence of amplification product in the sample, while the absence of FRET is (usually) indicative of the absence of amplification product in the sample. Alternatively a single hybridization probe is used having on one of its ends a donor fluorescent moiety and on the other end an acceptor fluorescent moiety.

In another aspect, the present invention provides an accurate screening method for carriers of a genetic polymorphism within two or more closely linked, homologous genes in a sample using a method according to the invention. Thus the present invention also relates to a method of diagnosing an individual by identifying his or her genotype.

For example, in one specific embodiment the present invention provides herein methods for detection and quantitation of a genetic polymorphism occurring within the thalassemia genes α1 and α2 in a sample, using the above RT-PCR techniques, thereby determining the clinical relevant classification of the α-thalassemias (FIG. 3). Thus, the present invention also provides an accurate screening method for carriers of (deletional) α-thalassemia.

In a specific embodiment the method for accurate quantitative detection of the α gene(s) in a biological sample comprises the steps of:
(i) amplifying a first portion of the sample with a pair of forward and reverse primers specific for the head region of α1;
(ii) amplifying a second portion of the sample with a pair of forward and reverse primers specific for the head region of α2;
(iii) amplifying a third portion of the sample with a pair of forward and reverse primers specific for the tail region of α1;
(iv) amplifying a fourth portion of the sample with a pair of forward and reverse primers specific for the tail region of α2; and
(v) detecting and quantifying amplification products relative to a control product.

In one embodiment, the control product is an endogeneous control product, preferably the β-gene amplification product. Thus, the method of the invention may include a pair of forward and reverse primers specific for the β-globin, i.e. that are capable of specifically hybridizing to and amplifying a sequence of the β-globin gene as identified by GenBank Accession No. U01317. In one embodiment the pair of forward and reverse primers specific for the β-globin are included in each amplification reaction (i) to (iv), in another embodiment a separate RT-PCR reaction is performed using the forward and reverse primers specific for the β-globin.

In another embodiment, the head and tail regions of α1, which are defined as the 5'- and the 3'-terminal regions of α1, respectively, preferably correspond to about nucleotides 163708 to nucleotides 167099 of the 5'-sequence (i.e. head region) and to about nucleotides 167099 to nucleotides 170335 of the 3'-sequence (i.e. tail region) of the α-globin gene cluster, e.g. as identified in GenBank Accession No. AE006462. In another embodiment, the head and tail regions of α2, which are defined as the 5'- and the 3'-terminal regions of α2, respectively, preferably correspond to about nucleotides 158640 to nucleotides 162875 of the 5'-sequence (i.e. head region) and to about nucleotides 162875 to nucleotides 166679 of the 3'-sequence (i.e. tail region) of the α-globin gene cluster, e.g. as identified in GenBank Accession No. AE006462.

In a further embodiment the detecting step is performed using at least one labelled hybridization probe. In a preferred embodiment, a pair of probes is used, wherein a first probe has a label at its 3' end and a second probe has a label at its 5'-end. In another embodiment one probe is being used having a label each at its 3' and its 5' end.

Preferred pairs of probes are SEQ ID No: 9 and 10 for the head region of α1, 11 and 12 for the tail region of α1, 13 and 14 for the head region of α2, and 15 and 16 for the tail region of α2.

In a further embodiment the positions of the primers are chosen such to obtain an amplicon having a length of 150 to 250 bp.

Along with the method, the present invention also provides for specific oligonucleotides to be used as primers in the methods according to the invention.

Thus, in a further specific embodiment the pairs of forward and reverse primers specific for the head- or tail-regions of each of α1 and α2 are each a nucleic acid sequence between 10 and about 100 nucleotides, preferably 10 and about 50 nucleotides, more preferably about 10 and 30 nucleotides, most preferably between 14 and 22 nucleotides in length. Such oligonucleotides or PCR primer pairs may be derived from the known sequence of the α-globin gene cluster set forth in GenBank Accession No. AE006462 by using computer programs intended for that purpose such as LightCycler Probe Design Software 2.0 (Roche Applied Science, Roche Diagnostics GmbH, Mannheim, Germany) or Primer (Version 0.5, (c) 1991, Whitehead Institute for Biomedical Research, Cambridge, Mass.) or any other program and are of specific composition and length such that they are capable of hybridizing under high and/or very high stringency conditions to their target site. Likewise the oligonucleotides or PCR primer pairs for the control gene sequence of choice (e.g. the β-globin gene sequence), may be derived from the known sequence of the β-globin gene set forth in GenBank Accession No: U01317.

Thus, in one embodiment, the pair of forward and reverse primers specific for the head and tail region of α1 comprise a nucleic acid sequence specific for about nucleotides 163708 to nucleotides 167099 of the 5'-sequence (i.e. head region) and for about nucleotides 167099 to nucleotides 170335 of the 3'-sequence (i.e. tail region) of the α-globin gene cluster (as identified by GenBank Accession No. AE006462). In another embodiment, the pair of forward and reverse primers specific for the head and tail region of α2 comprise a nucleic acid sequence specific for about nucleotides 158640 to nucleotides 162875 of the 5'-sequence (i.e. head region) and to about nucleotides 162875 to nucleotides 166679 of the 3'-sequence (i.e. tail region) of the α-globin gene cluster (as identified by GenBank Accession No. AE006462).

Thus, in one specific embodiment the pair of forward and reverse primers specific for the head and tail regions of α1 comprise a nucleic acid sequence at least 95% identical to the nucleotide sequences set forth as SEQ ID NO: 1 (α1-head-forward) and 4 (α1-head-reverse) corresponding to positions 165586-165607 and 165737-165752, and SEQ ID NO: 3 (α1-tail-forward) and 2 (α1-tail-reverse), corresponding to positions 168339-168354 and 168476-168494, respectively. The pair of forward and reverse primers specific for the head and tail regions of α2 comprise a nucleic acid sequence at least 95% identical to the nucleotide sequence set forth as SEQ ID NO: 5 (α2-head-forward) and 6 (α2-head-reverse) corresponding to positions 161708-161723 and 161899-161914, and SEQ ID NO: 7 (α2-tail-forward) and 8 (α2-tail-reverse) corresponding to positions 163584-163603 and 1637439-163755, respectively.

It is understood that the invention further encompasses nucleic acid molecules that differ from the nucleotide sequences shown in SEQ ID NO: 1 to 8, due to the degeneracy of the genetic code.

It is also understood that oligonucleotides consisting of SEQ ID NO:1 to 8 of the present invention may contain minor deletions, additions and/or substitutions of nucleic acid bases, to the extent that such alterations do not negatively affect the yield or product obtained to a significant degree.

In a further specific embodiment, the primer(s) comprise a label, e.g. a fluorescent, biotin, enzymatic, chemical or radio-label, preferably a fluorescent label, or additional derivatization as defined hereinabove necessary for a use in RT PCR, i.e. to stabilize amplification products or to enhance fragment separation making amplicon discrimination, identification and quantification more accurate.

Methods for preparing and using primers are described in, for example, Sambrook et al. (1989) Molecular Cloning: A Laboratory Manual, Cold Spring Harbor, N.Y.; Ausubel et al. (1987) Current Protocols in Molecular Biology, Greene Publ. Assoc. Wiley-Intersciences.

Thus in a more specific embodiment, the present invention provides a method for detecting a genetic polymorphism within the thalassemia genes α1 and α2, comprising the steps of:

(i) obtaining a genomic sample, (ii) subjecting said sample to four separate amplification reactions by RT-PCR using
 (a) in a first reaction a primer pair that specifically hybridizes under conditions suitable for a PCR with a sequence between about nucleotides 163708 to nucleotides 167099 of the α-globin gene cluster as identified in GenBank Accession No. AE006462 (sequence head α1), preferably a primer pair such as SEQ ID NO: 1 and 2 (primer head α1),
 (b) In a second reaction a primer pair having a sequence that specifically hybridizes under conditions suitable for a PCR with a sequence between about nucleotides 158640 to nucleotides 162875 of the α-globin gene cluster as identified in GenBank Accession No. AE006462 (sequence head α2), preferably a primer pair such as SEQ ID NO: 5 and 6 (primer head α2),
 (c) In a third reaction a primer pair that specifically hybridizes under conditions suitable for a PCR with a sequence between about nucleotides 167099 to nucleotides 170335 of the α-globin gene cluster as identified in GenBank Accession No. AE006462 (sequence tail α1), preferably a primer pair such as SEQ ID NO: 3 and 4 (primer tail α1),
 (d) In a fourth reaction a primer pair having a sequence that specifically hybridizes under conditions suitable for a PCR with a sequence between about nucleotides 162875 to nucleotides 166679 of the α-globin gene cluster as identified in GenBank Accession No. AE006462 (sequence tail α2), preferably a primer pair such as SEQ ID NO: 7 and 8 (primer tail α2), and (iii) detecting and quantifying the amplification products relative to a control product.

In one embodiment, the control product is an endogenous control product, preferably the β-gene amplification product. Thus, the method of the invention may include adding a primer pair for an endogenous control sequence, e.g. a primer pair that specifically hybridizes under conditions suitable for a PCR with a sequence of the β-globin gene as identified in GenBank Accession No. U01317, preferably a primer pair such as SEQ ID NO: 17 and 18 (primer β-globin gene), to each of the amplification reactions.

Alternatively, the method of the invention may include a further step which comprises subjecting said sample to a fifth separate amplification reaction by RT PCR using a primer pair that specifically hybridizes under conditions suitable for a PCR with a sequence of the β-globin gene as identified in GenBank Accession No. U01317, preferably a primer pair such as SEQ ID NO: 17 and 18 (primer β-globin gene).

Thus in one preferred embodiment, the present invention provides a method for detecting a genetic polymorphism within the thalassemia genes α1 and α2, comprising the steps of:

(i) obtaining a genomic sample,
(ii) subjecting said sample to four separate amplification reactions by RT-PCR using
- (a) in a first reaction a primer pair that specifically hybridizes under conditions suitable for a PCR with a sequence between about nucleotides 163708 to nucleotides 167099 of the α-globin gene cluster as identified in GenBank Accession No. AE006462 (sequence head α1), preferably a primer pair such as SEQ ID NO: 1 and 2 (primer head α1), and a primer pair that specifically hybridizes under conditions suitable for a PCR with a sequence of the β-globin gene as identified in GenBank Accession No. U01317, preferably a primer pair such as SEQ ID NO: 17 and 18 (primer β-globin gene),
- (b) In a second reaction a primer pair having a sequence that specifically hybridizes under conditions suitable for a PCR with a sequence between about nucleotides 158640 to nucleotides 162791 of the α-globin gene cluster as identified in GenBank Accession No. AE006462 (sequence head α2), preferably a primer pair such as SEQ ID NO: 5 and 6 (primer head α2), and a primer pair that specifically hybridizes under conditions suitable for a PCR with a sequence of the β-globin gene as identified in GenBank Accession No. U01317, preferably a primer pair such as SEQ ID NO: 17 and 18 (primer β-globin gene),
- (c) In a third reaction a primer pair that specifically hybridizes under conditions suitable for a PCR with a sequence between about nucleotides 167099 to nucleotides 170335 of the α-globin gene cluster as identified in GenBank Accession No. AE006462 (sequence tail α1), preferably a primer pair such as SEQ ID NO: 3 and 4 (primer tail α1), and a primer pair that specifically hybridizes under conditions suitable for a PCR with a sequence of the β-globin gene as identified in GenBank Accession No. U01317, preferably a primer pair such as SEQ ID NO: 17 and 18 (primer β-globin gene),
- (d) In a fourth reaction a primer pair having a sequence that specifically hybridizes under conditions suitable for a PCR with a sequence between about nucleotides 162791 to nucleotides 166679 of the α-globin gene cluster as identified in GenBank Accession No. AE006462 (sequence tail α2), preferably a primer pair such as SEQ ID NO: 7 and 8 (primer tail α2), and a primer pair that specifically hybridizes under conditions suitable for a PCR with a sequence of the β-globin gene as identified in GenBank Accession No. U01317, preferably a primer pair such as SEQ ID NO: 17 and 18 (primer β-globin gene), and (iii) detecting and quantifying the amplification products relative to a control product.

In another preferred embodiment, the present invention provides a method for detecting a genetic polymorphism within the thalassemia genes α1 and α2, comprising the steps of:
(i) obtaining a genomic sample,
(ii) subjecting said sample to five separate amplification reactions by RT-PCR using
- (a) in a first reaction a primer pair that specifically hybridizes under conditions suitable for a PCR with a sequence between about nucleotides 163708 to nucleotides 167099 of the α-globin gene cluster as identified in GenBank Accession No. AE006462 (sequence head α1), preferably a primer pair such as SEQ ID NO: 1 and 2 (primer head α1),
- (b) In a second reaction a primer pair having a sequence that specifically hybridizes under conditions suitable for a PCR with a sequence between about nucleotides 158640 to nucleotides 162791 of the α-globin gene cluster as identified in GenBank Accession No. AE006462 (sequence head α2), preferably a primer pair such as SEQ ID NO: 5 and 6 (primer head α2),
- (c) In a third reaction a primer pair that specifically hybridizes under conditions suitable for a PCR with a sequence between about nucleotides 167099 to nucleotides 170335 of the α-globin gene cluster as identified in GenBank Accession No. AE006462 (sequence tail α1), preferably a primer pair such as SEQ ID NO: 3 and 4 (primer tail α1),
- (d) In a fourth reaction a primer pair having a sequence that specifically hybridizes under conditions suitable for a PCR with a sequence between about nucleotides 162791 to nucleotides 166679 of the α-globin gene cluster as identified in GenBank Accession No. AE006462 (sequence tail α2), preferably a primer pair such as SEQ ID NO: 7 and 8 (primer tail α2),
- (e) In a fifth reaction a primer pair having a sequence that specifically hybridizes under conditions suitable for a PCR with a sequence of the β-globin gene as identified in GenBank Accession No. U01317, preferably a primer pair such as SEQ ID NO: 17 and 18 (primer β-globin gene), and (iii) detecting amplification products for each of the steps (a) through (d) and an amplification control product for step (e), and quantifying the amplification products relative to the amplification control product.

Relative quantification according to step (iii) gives a ratio, wherein the ratio allows to identify a carrier of α-thalassemia.

In a further aspect the present invention provides uses for a method according to the invention, for example using the method for determining a genotype of two or more, closely linked, homologous genes in a sample by (i) amplifying head and tail region of each of the two or more, closely linked, homologous genes in separate amplification reactions using a pair of forward and reverse primers, and (ii) detecting and quantifying amplification products relative to a control product.

In a further aspect the invention provides kits for the differential quantitative detection of two or more closely linked, homologous genes in a sample which comprise reagents that can be used in practicing the methods disclosed herein. Thus a kit according to the invention comprises in separate compartments (a) a pair of forward and reverse primers specific for the head region of each of said two or more, closely linked, homologous genes and (b) a pair of forward and reverse primers specific for the tail region of each of said two or more, closely linked, homologous genes. The kit may further include one or more appropriately labelled hybridisation probes for detection and a primer pair capable of hybridizing to and amplifying a control sequence, preferably an endogeneous control sequence of choice, for relative quantitation. The kits may also include further reagents for amplification, reaction control reagents, buffers and instructions for performing assays and for interpreting results.

In a specific embodiment, a kit for the differential quantitative detection of the thalassemia genes α1 and α2 in a sample, comprises in separate compartments pairs of forward and reverse primers capable of specifically hybridizing to and amplifying the head and tail regions of the α1 and α2 genes according to the invention. The kit may further include one or more appropriately labelled hybridisation probes for detection and a primer pair capable of hybridizing to and amplifying a control sequence, preferably an endogenous control sequence of choice, e.g. the β-globin gene sequence.

In a further aspect the methods of the invention may be performed using (micro) arrays. The methods of the invention as described above allows for parallel processing of a large number of genomic nucleic acid samples and may be applied in automated robotic platforms. Such system usually comprises a microplate with an array of wells arranged in rows and columns, wherein each well would be assigned to a specific amplification reaction, e.g. a microplate with an array of ninety-six wells allows a parallel processing of a large number of hybridisations resulting in a very efficient high-throughput analysis.

EXAMPLES

Materials and Methods

Samples.

Blood samples from patients with α-thalassemia were collected in the routine laboratory for haemoglobinopathies. Samples from healthy individuals were used as controls.

DNA Extraction.

Genomic DNA was extracted from peripheral human blood using a manual (Qiagen Mini Kit, Qiagen AG, Basel, Switzerland) or automated (MagnaPure, Roche Diagnostics AG, Rotkreuz, Switzerland) DNA-extraction method. Photometric quantification of genomic DNA was performed on NanoDrop (Roche Technologies, inc. Wilmington, USA) and only samples with a 260 nm:280 nm-ratio in a defined range were selected for the experiments. DNA was adjusted to the desired concentration (10 ng/µl) and either stored at 4° C. or used immediately.

Real-Time (RT) PCR.

All RT-PCR experiments were performed on the LightCycler System (Roche Diagnostics AG, Rotkreuz, Switzerland). After initial denaturation for 10 min at 95° C., amplification was performed using the following cycling conditions: 40 cycles for 10 min at 95° C., 10 min at 55° C. and 10 min at 72° C., and one cycles for cooling to 40° C.

Fluorescence intensity was monitored once per cycle after each elongation phase. A melting curve was produced after a fully completed run starting at 55° C. heating up to 99° C. at a transition rate of 0.1° C./s.

Primer Design.

Primers and Probes were designed using LightCycler Probe Design Software 2.0 (Roche Applied Science, Roche Diagnostics GmbH, Mannheim, Germany). All the primers fulfil the following criteria: the amplification products are 200-300 bp, melting temperatures are 45-65° C., lack of stable dimer formation and stable hair-pin structure formation. Modification of the hybridization probes included phosphate (PH) and labelling with 3'-fluorescein (FL) and 5'-LightCycler Red 640 (LC), respectively.

The following table 1 summarizes a selection of primers and probes that were used for the amplification of four different loci on the α-globin-gene and one locus on the β-globin-gene, which was chosen as reference gene in this specific case:

TABLE 1

| Primer/Probe | Name | Sequence (with/without labels) | SEQ ID No | Base position |
|---|---|---|---|---|
| α1-head-forward | α1h-F | 5'-CCTCCTCCACCTAATACATATC-3' | 1 | 165586-165607 |
| α1-head-reverse | α1h-R | 5'-AggTAggCAgTCCTCT-3' | 2 | 165737-165752 |
| α1-tail-forward | α1t-F | 5'-CTggCCCTCAACTgAT-3' | 3 | 168339-168354 |
| α1-tail-reverse | α1t-R | 5'-AAATAACgAAgACACCgTC-3' | 4 | 168476-168494 |
| α2-head-forward | α2h-F | 5'-gACggggTTTCTCCAT-3' | 5 | 161708-161723 |
| α2-head-reverse | α2h-R | 5'-ggTgAggAAggAAggg-3 | 6 | 161899-161914 |
| α2-tail-forward | α2t-F | 5'-CTCCAAATACCgTTAAgCTg-3' | 7 | 163584-163603 |
| α2-tail-reverse | α2t-R | 5'-ATTgTTggCACATTCCg-3' | 8 | 163739-163755 |
| α1-head-P1 | α1h-P1 | 5'-ACTAACCCTggTCACCTTgAA-FL | 9 | 165640-165660 |
| α1-head-P2 | α1h-P2 | Red640-CCTCgTCCACACCTCCAg-Ag-PH | 10 | 165663-165680 |
| α1-tail-P1 | α1t-P1 | 5'-TCACCCTTggTAAACACCTATggC-FL | 11 | 168386-168409 |
| α1-tail-P2 | α1t-P2 | LC Red640-gCCCTCTgCCTgCgTT-PH | 12 | 168412-168427 |
| α2-head-P1 | α2h-P1 | 5'-ggTCTCgAACTCCCgACC-FL | 13 | 161736-161753 |

TABLE 1-continued

| Primer/Probe | Name | Sequence (with/without labels) | SEQ ID No | Base position |
|---|---|---|---|---|
| α2-head-P2 | α2h-P2 | 5'-LC Red640-AgCTgATCCACCCgCC-PH | 14 | 161756-161771 |
| α2-tail-P1 | α2t-P1 | 5'-CCTTCCTggTCTTTgAATAAAgTTgAg-FL | 15 | 163673-163700 |
| α2-tail-P2 | α2t-P2 | 5'-LC Red640-ggCAgCAgCCTgTgTgT-PH | 16 | 163703-163719 |
| β-forward | β-F | 5'-ACACAACTgTgTTCACTAgC-3' | 17 | 4035529-4035510 |
| β-reverse | β-R | 5'-CAACTTCATCCACgTTCACC-3' | 18 | 4035420-4035439 |
| β-P1 | β-P1 | 5'-AAACAgACACCATggTgCACCTgA-CTCCTgAggA-FL | 19 | 4035503-4035470 |
| β-P2 | β-P2 | 5'-LC Red640-AAgTCT-gCCgTTACTgCCCTgTggggCAA-PH | 20 | 4035468-4035440 |

Example 1

Optimization of Quantitative RT PCR

Optimization of RT PCR for quantification was carried out using the DNA-intercalating fluorescent dye SYBR-green (to account for potential fluorescence signals arising due to non-specific double-stranded products with intercalating dyes). The reaction mixture contained 1× LightCycler FastStart DNA Master SYBR Green I (Roche Diagnostics AG, Rotkreuz, Switzerland), 1 mM MgCl$_2$, 0.5 μM forward and reverse primer for either of the head or tail region of α1 (SEQ ID No. 1-4) or of the head or tail region of α2 (SEQ ID No. 5-8), or 1 μM forward and reverse primer specific for the β-globin gene (SEQ ID No. 17-18). The PCR reactions were performed in a total volume of 10 μl by distributing 8 μl aliquots of the master mix into the capillaries, followed by the addition of 2 μl of DNA containing 10 ng/μl.

Example 2

Based on the optimized reaction conditions according to Example 1, the method was adapted for the use of labeled probes. Four different reaction mixtures were prepared, whereas all of them contained 1× LightCycler FastStart DNA Master HybProbe (Roche) and 1.5 mM MgCl$_2$ in addition to the relative primers and probes.
1. 0.5 mM α1 head-forward primer SEQ ID No. 1 and α1 head-reverse primer SEQ ID No. 2, 0.5 mM fβ-globin forward and reverse primers SEQ ID No. 17 and 18, 0.2 mM of the FL-labeled hybridization probes and 0.3 mM of the LC-labeled hybridization probes for both the α1 head gene region (SEQ ID No. 9 and 10) and the β-globin gene region (SEQ ID No. 19 and 20)
2. 0.5 mM α2 head-forward primer SEQ ID No. 5 and α2 head-reverse primer SEQ ID No. 6, 0.5 mM forward and reverse β-globin primers SEQ ID No. 17 and 18, 0.2 mM of the FL-labeled hybridization probes and 0.3 mM of the LC-labeled hybridization probes for both the α2 head gene region (SEQ ID No. 13 and 14) and the β-globin gene region (SEQ ID No. 19 and 20)
3. 0.5 mM α1 tail-forward primer SEQ ID No. 3 and α1 tail-reverse primer SEQ ID No. 4, 0.5 mM β-globin forward and reverse primers SEQ ID No. 17 and 18, 0.2 mM of the FL-labeled hybridization probes and 0.3 mM of the LC-labeled hybridization probes for both the α1 tail gene region (SEQ ID No. 11 and 12) and the β-globin gene region (SEQ ID No. 19 and 20)
4. 0.5 mM α2 tail-forward primer SEQ ID No. 7 and α2 tail-reverse primer SEQ ID No. 8, 0.5 mM β-globin forward and reverse primers SEQ ID No. 17 and 18, 0.2 mM of the FL-labeled hybridization probes and 0.3 mM of the LC-labeled hybridization probes for both the α2 tail gene region (SEQ ID No. 15 and 16) and the β-globin gene region (SEQ ID No. 19 and 20)

PCR reaction is performed in a total volume of 10 ml, whereof 8 ml were aliquots of the master mix, followed by the addition of 2 ml of DNA containing 10 ng/ml.

After initial denaturation for 10 min at 95° C., amplification was performed using the following cycling conditions: 45 cycles for 10 min at 95° C., 10 min at 55° C. and 10 min at 72° C., and one cycle for cooling to 40° C. Fluorescence intensity was monitored once per cycle after each elongation phase. A melting curve was produced after a fully completed run starting at 55° C. heating up to 95° C. at a transition rate of 0.1° C./s.

Analysis The specificity of the obtained amplicons was controlled trough melting curves, gel electrophoresis and/or sequencing. The amplification products were analyzed using the automated method of the LightCycler data analysis software (Version 4.0, Roche). The ct-signal-ratio between the α-globin-gene and the β-globin reference-gene was determined permitting to identify the relative quantity of the amplicated genes (the parameter ct or "threshold cycle" is defined as the cycle number at which the fluorescence emission exceeds the fixed threshold, which is set significantly above the baseline). Through analysis of the obtained ratio pattern the genotype of the patient was defined (Table 2, FIG. 4). FIG. 4 shows the various possible haplotype combinations of α-gene deletions and triplications and the corresponding genomic copy number for head and tail regions of the α1 and α2-genes. Only in three circumstances (shaded combinations) is an analysis of head as well as tail regions of the α-genes necessary to define the exact genotype. For all other combinations the analysis of the head region is sufficient. Statistical analysis was performed with the SPSS software (Version 10.0 for Windows).

In cases with positive screening results, the detection of an aberrant ratio pattern, obtained by the described method, additional specific methods such as sequencing were performed to obtain detailed definition of the genetic defect.

TABLE 2

Quantification and Identification of genotype of samples (i) to (v) using the primers and probes according to Example 2:

| Ex. 2 | Ct α1h | Ct α1t | Ct α2h | Ct α2t | Ctβ2t | Ct ratios calc | genotype |
|---|---|---|---|---|---|---|---|
| i | 27 | 27 | 27 | 27 | 27 | 1 | wt |
| ii | 28 | 27 | 27 | 28 | 27 | α1h/b = 1.04<br>α1t/b = 1<br>α2h/b = 1<br>α2t/b = 1.04 | $-\alpha^{3.7\,kb}$ heterozygot |
| iii | n.d. | 27 | 27 | n.d. | 27 | α1h/b = 0<br>α1t/b = 1<br>α2h/b = 1<br>α2t/b = 0 | $-\alpha^{3.7\,kb}$ homozygot |
| iv | 28 | 28 | 28 | 28 | 27 | α1h/b = 1.04<br>α1t/b = 1.04<br>α2h/b = 1.04<br>α2t/b = 1.04 | $\alpha^0$ heterozygot |
| v | 27 | 27 | n.d. | n.d. | 27 | α1h/b = 1<br>α1t/b = 1<br>α2h/b = 0<br>α2t/b = 0 | $-\alpha^{4.2\,kb}$ homozygote | n.d. = not detectable

These results unambiguously indicate that the individual of sample (i) is a healthy individual whereas the individuals of samples (ii) to (v) are carriers of different deletions in the α-globin gene cluster.

The invention claimed is:

1. A method of screening for an α-thalassemia carrier comprising the steps of:
   (i) obtaining a genomic sample,
   (ii) subjecting said sample to four separate amplification reactions by RT-PCR using
   (a) a primer pair that specifically hybridizes under conditions suitable for a PCR with a sequence between about nucleotides 163708 to nucleotides 167099 of the α-globin gene cluster as identified in GenBank Accession No. AE006462,
   (b) a primer pair having a sequence that specifically hybridizes under conditions suitable for a PCR with a sequence between about nucleotides 158640 to nucleotides 162791 of the α-globin gene cluster as identified in GenBank Accession No. AE006462,
   (c) a primer pair that specifically hybridizes under conditions suitable for a PCR with a sequence between about nucleotides 167099 to nucleotides 170335 of the α-globin gene cluster as identified in GenBank Accession No. AE006462,
   (d) a primer pair having a sequence that specifically hybridizes under conditions suitable for a PCR with a sequence between about nucleotides 162791 to nucleotides 166679 of the α-globin gene cluster as identified in GenBank Accession No. AE006462, and
   (iii) detecting and quantifying the amplification products relative to a control product,
   wherein the pair of primers comprises:
   in step a), a primer pair comprising (the sequences comprising/consisting of) SEQ ID NO: 1 and 2;
   in step b), a primer pair comprising SEQ ID NO: 3 and 4;
   in step c), a primer pair comprising SEQ ID NO: 5 and 6; and
   in step d), a primer pair comprising SEQ ID NO: 7 and 8.

2. The method of claim 1, wherein the pairs of primers are immobilized in an array.

3. A set of pairs of forward and reverse primers and pairs of hybridization probes, for screening for an α-thalassemia carrier by RT-PCR through the amplification of
   (i) the head region of α1 comprising a nucleic acid 10 to 100 nucleotides in length capable of hybridizing under high stringency conditions to about nucleotides 163708 to 167099 of the α-globin gene cluster as set forth in GenBank Accession No. AE006462,
   (ii) the tail region of α1 comprising a nucleic acid 10 to 100 nucleotides in length capable of hybridizing under high stringency conditions to about 167099 to 170335 of the α-globin gene cluster as set forth in GenBank Accession No. AE006462, (iii) the head of α2 comprising a nucleic acid 10 to 100 nucleotides in length capable of hybridizing under high stringency conditions to about nucleotides 158640 to 162791 of the α-globin gene cluster as set forth in Gen-Bank Accession No. AE006462, and (iv) the tail region of α2 comprising a nucleic acid 10 to 100 nucleotides in length capable of hybridizing under high stringency conditions to about 162791 to 166679 of the α-globin gene cluster as set forth in GenBank Accession No. AE006462, wherein the pair of primers an the pairs of hybridization probes comprise:

in step i), a primer pair comprising SEQ ID NO: 1 and 2, and a hybridisation probe pair comprising SEQ ID 9 and 10;

in step ii), a primer pair comprising SEQ ID NO: 3 and 4, and a hybridisation probe pair comprising SEQ ID 11 and 12;

in step iii), a primer pair comprising SEQ ID NO: 5 and 6, and a hybridisation probe pair comprising SEQ ID 13 and 14; and in step iv), a primer pair comprising SEQ ID NO: 7 and 8, and a hybridisation probe pair comprising SEQ ID 15 and 16.

4. A kit for screening for an α-thalassemia carrier by RT-PCR, comprising in separate compartments (a) a primer pair that specifically hybridizes under conditions suitable for a PCR with a sequence between about nucleotides 163708 to nucleotides 167099 of the α-globin gene cluster as identified in GenBank Accession No. AE006462 and a hybridisation probe pair, (b) a primer pair having a sequence that specifically hybridizes under conditions suitable for a PCR with a sequence between about nucleotides 158640 to nucleotides 162791 of the α-globin gene cluster as identified in GenBank Accession No. AE006462 and a hybridisation probe pair, (c) a primer pair that specifically hybridizes under conditions suitable for a PCR with a sequence between about nucleotides 167099 to nucleotides 170335 of the α-globin gene cluster as identified in GenBank Accession No. AE006462 and a hybridisation probe pair, (d) a primer pair having a sequence that specifically hybridizes under conditions suitable for a PCR with a sequence between about nucleotides 162791 to nucleotides 166679 of the α-globin gene cluster as identified in GenBank Accession No. AE006462 and a hybridisation probe pair wherein the primer pair and the hybridisation probe pair comprises:

in compartment (a), a primer pair comprising SEQ ID NO: 1 and 2, and a hybridisation probe pair comprising SEQ ID 9 and 10;

in compartment (b), a primer pair comprising SEQ ID NO: 3 and 4, and a hybridisation probe pair comprising SEQ ID 11 and 12;

in compartment (c), a primer pair comprising SEQ ID NO: 5 and 6, and a hybridisation probe pair comprising SEQ ID 13 and 14; and in compartment (d), a primer pair comprising SEQ ID NO: 7 and 8, and a hybridisation probe pair comprising SEQ ID 15 and 16.

5. The method according to claim 1, wherein the sample is genomic DNA.

6. The method according to claim 1, wherein the control product is obtained by amplifying an endogenous control sequence (i) in each of the separate amplification reactions or (ii) in a separate amplification reaction, using a pair of forward and reverse primers specific for said endogenous control sequence.

* * * * *